United States Patent [19]
Casas et al.

[11] Patent Number: 6,100,388
[45] Date of Patent: Aug. 8, 2000

[54] LACTOBACILLI HARBORING AGGREGATION GENE AS A VACCINE DELIVERY VEHICLE

[75] Inventors: Ivan Casas, Raleigh, N.C.; Hans Jonsson, Uppsala, Sweden; Bo Möllstam, Lerum, Sweden; Stefan Roos, Uppsala, Sweden

[73] Assignee: BioGaia Biologies AB, Stockholm, Sweden

[21] Appl. No.: 09/039,773

[22] Filed: Mar. 16, 1998

[51] Int. Cl.$^7$ .......................... C07H 21/04; C07H 21/02; C07H 21/00
[52] U.S. Cl. ...................... 536/23.5; 536/23.1; 536/23.4; 536/23.41
[58] Field of Search ................................. 536/23.1, 23.5, 536/23.41

[56] References Cited

U.S. PATENT DOCUMENTS

| | | |
|---|---|---|
| 5,534,253 | 7/1996 | Casas et al. . |
| 5,837,238 | 11/1998 | Casas et al. . |
| 5,851,794 | 12/1998 | Guss et al. . |

FOREIGN PATENT DOCUMENTS

| | | |
|---|---|---|
| 9507300 | 3/1995 | WIPO . |
| WO 96 32486 | 10/1996 | WIPO . |
| WO 97 09437 | 3/1997 | WIPO . |
| 9947657 | 9/1999 | WIPO . |

OTHER PUBLICATIONS van der Lelie et al. Applied & Environmental Microbiology 57/1: 201–206, Jan. 1991.

Roos et al. FEMS Microbiol. Lett. 144:33–38, 1996.

Takahashi et al. Biosci. Biotech. Biochem. 60/9:1434–1438, 1996.

Patti et al. JBC, 267/7:4766–4772, 1992.

Jonsson et al. BBA 1249:65–71, 1995.

Kmet et al., FEMS Immunol. & Med. Microbiol., 19:111–114, 1997.

Roos, et al. "Autoaggregation of *Lactobacillus reuteri* is mediated by a putative DEAD–box helicase," XP002117044, Chemical Abstracts, abstract No. 85226, vol. 131 1999, and Mol. Microbiol. vol. 32, No. 2, 1999 pp. 427–436.

Wells, et al. "Lactic Acid Bacteria as vaccine delivery vehicles," Antonie Van Leeuwenhoek, vol. 70, 1996, pp. 317–3330, XP002117043.

*Primary Examiner*—Nita Minnifield
*Attorney, Agent, or Firm*—Standley & Gilcrest LLP

[57] ABSTRACT

Live vaccines and methods for preparing the vaccines useful in protecting a host from infection by a pathogenic microorganism are provided. Vaccines are prepared from live Lactobacillus cells which have been transformed using DNA technology to express heterologous antigens of pathogenic microorganisms or other suitable biological material. Genes encoding antigenic determinants pathogenic in the mammalian gastrointestinal tract are inserted into expression cassettes and fused with genes encoding an aggregation factor and/or a mucin binding factor. The inserted genes are shown to transform *L. reuteri* cells. The aggregation enhancing and mucin binding genes have been isolated and sequenced. The vaccine can be ingested orally in a pharmaceutical carrier or in milk products.

1 Claim, No Drawings

SEQUENCE LISTING (1) GENERAL INFORMATION:

(iii) NUMBER OF SEQUENCES:2

(2) INFORMATION FOR SEQ ID NO:1:

(i) SEQUENCE CHARACTERISTICS:
      (A) LENGTH:1800 base pairs
      (B) TYPE:Nucleic acid
      (C) STRANDEDNESS:Double
      (D) TOPOLOGY:Circular (ii) MOLECULE TYPE:Genomic DNA
      (A) DESCRIPTION:Genomic DNA sequence and deduced amino
          acid sequence of bacterial aggregation
          protein (iii) HYPOTHETICAL:No (iv) ANTI-SENSE:Yes (v) FRAGMENT TYPE:

(vi) ORIGINAL SOURCE:
      (A) ORGANISM:Lactobacillus reuteri sp
      (B) STRAIN:1063
      (C) CELL TYPE:Unicellular organism (xi) SEQUENCE DESCRIPTION: SEQ ID NO:   1:

```
ATTAATTGCC GATCTTACGG CTACTTTGAC AGGTGAGGAT ATTGTTCTAT                 50

TGAAAGCAAG CCATGGTATT CACCTAGAAG AAGTCTTGAC GGCATTAAAA                100

GCAGAATAGT TAATATATTT GCCAGTCGAT TACTGATGCT TATATCATGA                150

ATCGACTGGT CATTTTTAGG AGGAAAATTT TTG AAG TTT AGT GAA TTA              198
                                  Met Lys Phe Ser Glu Leu
                                   1               5

GGC TTA TCC GAT AGC CTA TTA AAA GCA ATC AAA CGG AGC GGA                240
Gly Leu Ser Asp Ser Leu Leu Lys Ala Ile Lys Arg Ser Gly
             10                  15                  20

TAC GAA GAA GCA ACA CCA ATT CAA GAA CAA ACG ATT CCA ATG                282
Tyr Glu Glu Ala Thr Pro Ile Gln Glu Gln Thr Ile Pro Met
                 25                  30

GTT CTT GAG GGT AAG GAT GTT ATT GGT CAA GCA CAG ACT GGA                324
Val Leu Glu Gly Lys Asp Val Ile Gly Gln Ala Gln Thr Gly
 35                  40                  45

ACT GGT AAG ACG GCT GCT TTT GGG TTG CCA ATT ATT GAA AAC                366
Thr Gly Lys Thr Ala Ala Phe Gly Leu Pro Ile Ile Glu Asn
     50                  55                  60

GTT GAT ACT GAA AAT CCC AAT ATT CAA GCA ATT ATC ATT TCA                408
Val Asp Thr Glu Asn Pro Asn Ile Gln Ala Ile Ile Ile Ser
             65                  70                  75
```

-continued

```
CCA ACA CGT GAA TTA GCG ATC CAG ACC CAA GAA GAA CTT TAT        450
Pro Thr Arg Glu Leu Als Ile Gln Thr Gln Glu Glu Leu Tyr
            80                  85                  90

CGT CTA GGT AAA GAT AAA CAT GTT CGC GTG CAG GTA GTC TAT        492
Arg Leu Gly Lys Asp Lys His Val Arg Val Gln Val Val Tyr
                95                  100

GGT GGG GCA GAT ATT CGG CGC CAA ATT AAG AGC TTG AAA CAA        534
Gly Gly Ala Asp Ile Arg Agr Gln Ile Lys Ser Leu Lys Gln
105                 110                 115

CAC CCC CAA ATT CTC GTG GGG ACC CCT GGA CGG TTA CGT GAC        576
His Pro Gln Ile Leu Val Gly Thr Pro Gly Arg Leu Arg Asp
    120                 125                 130

CAT ATT AAC CGT CAT ACA GTT AAA CTT GAC CAC ATT AAG ACC        618
His Ile Asn Arg His Thr Val Lys Leu Asp His Ile Lys Thr
                135                 140                 145

CTG GTT CTC GAT GAA GCA GAT GAA ATG CTA AAC ATG GGA TTC        660
Leu Val Leu Asp Glu Ala Asp Glu Met Leu Asn Met Gly Phe
            150                 155                 160

TTA GAA GAT ATT GAA TCC ATC ATC AAG GAA ACA CCA GAT GAT        702
Leu Glu Asp Ile Glu Ser Ile Ile Lys Glu Thr Pro Asp Asp
                165                 170

CGG CAA ACT TTG CTC TTC TCA GCA ACC ATG CCA CCA GAA ATC        744
Arg Gln Thr Leu Leu Phe Ser Ala Thr Met Pro Pro Glu Ile
175                 180                 185

AAG CGA ATT GGG GTT CAA TTT ATG TCT GAT CCG GAA ACT GTG        786
Lys Arg Ile Gly Val Gln Phe Met Ser Asp Pro Glu Thr Val
        190                 195                 200

CGG ATC AAG GCC AAG GAA TTG ACT ACT GAC TTA GTT GAT CAG        828
Arg Ile Lys Ala Lys Glu Leu Thr Thr Asp Leu Val Asp Gln
        205                 210                 215

TAC TAT GTT CGC GCT CGT GAC TAT GAA AAG TTT GAC ATC ATG        870
Tyr Tyr Val Arg Ala Arg Asp Tyr Glu Lys Phe Asp Ile Met
            220                 225                 230

ACC CGC TTA ATT GAT GTT CAA GAT CCT GAC TTA ACA ATT GTC        912
Thr Arg Leu Ile Asp Val Gln Asp Pro Asp Leu Thr Ile Val
                235                 240

TTT GGT CGG ACA AAG CGG CGG GTA GAT GAA TTG TCG AAG GGC        954
Phe Gly Arg Thr Lys Arg Arg Val Asp Glu Leu Ser Lys Gly
245                 250                 255

TTG ATT GCG CGT GGC TAC AAT GCA GCT GGT ATC CAT GGT GAC        996
Leu Ile Ala Arg Gly Tyr Asn Ala Ala Gly Ile His Gly Asp
    260                 265                 270

CTT ACT CAG GAT AAG CGT TCT AAG ATC ATG TGG AAG TTT AAG       1038
Leu Thr Gln Asp Lys Arg Ser Lys Ile Met Trp Lys Phe Lys
                275                 280                 285

AAC AAT GAA CTT GAT ATC TTA GTT GCA ACA GAT GTG GCT GCC       1080
Asn Asn Gly Leu Asp Ile Leu Val Ala Thr Asp Val Ala Ala
                290                 295                 300

CGG GGC TTA GAC ATT TCG GGG GTT ACG CAT GTT TAT AAT TAT       1122
Arg Gly Leu Asp Ile Ser Gly Val Thr His Val Tyr Asn Tyr
            305                 310

GAT ATT CCA TCT GAC CCA GAC AGC TAT GTT CAC CGG ATT GGC       1164
Asp Ile Pro Ser Asp Pro Asp Ser Tyr Val His Arg Ile Gly
315                 320                 325

CGA ACA GGA CGG GCC GGA CAT CAC GGG GTA TCT TTA ACC TTT       1206
Arg Thr Gly Arg Ala Gly His His Gly Val Ser Leu Thr Phe
    330                 335                 340

GTG ACT CCA AAT GAG ATG GAT TAC CTT CAT GAG ATT GAA AAA       1248
Val Thr Pro Asn Glu Met Asp Tyr Leu His Glu Ile Gly Lys
345                 350                 355
```

```
TTA ACC CGG GTA CGG ATG TTG CCA CTC AAG CCA CCA ACA GCT        1290
Leu Thr Arg Val Arg Met Leu Pro Leu Lys Pro Pro Thr Ala
            360                 365                 370

GAA GAA GCA TTT AAG GGT CAA GTA GCA TCG GCC TTT AAT GAT        1332
Glu Glu Ala Phe Lys Gly Gln Val Ala Ser Ala Phe Asn Asp
                375                 380

ATC GAT GAA TTA ATC GCG CAG GAT TCA ACT GAT CGT TAT GAA        1374
Ile Asp Glu Leu Ile Ala Gln Asp Ser Thr Asp Arg Tyr Glu
385                 390                 395

GAA GCC GCT GAA AAG CTA TTA GAA ACT CAT AAT GCA ACT GAC        1416
Glu Ala Ala Glu Lys Leu Leu Glu Thr His Asn Ala Thr Asp
        400                 405                 410

CTA GTA GCA GCA TTG TTA AAT AAC ATG ACG AAG GAA GCA GCG        1458
Leu Val Ala Ala Leu Leu Asn Ans Met Thr Lys Glu Ala Ala
            415                 420                 425

AGT GAG GTT CCC GTT AAG ATT ACC CCT GAG CGT CCC CTT CCA        1500
Ser Glu Val Pro Val Lys Ile Thr Pro Glu Arg Pro Leu Pro
                430                 435                 440

CGG CGT AAT AAG CGG AAT AAC CGT AAT GGC AAC CGC AAT AAC        1542
Arg Arg Asn Lys Arg Asn Asn Arg Asn Gly Asn Arg Asn Asn
                    445                 450

TCG CAT GGT GGC AAC CAC TAC CGG CGT AAG AAT TTC CGT CGT        1584
Ser His Gly Gly Asn His Tyr Arg Arg Lys Asn Phe Arg Arg
455                 460                 465

CAC CAA CAT GGC AGT CAT CGA AAT GAT AAC CAT GGG AAG AGC        1626
His Gln His Gly Ser His Arg Asn Asp Asp His Gly Lys Ser
        470                 475                 480

CAT TCC AGT CGT CAT TCA TTT AAT ATT CGG CAC CGG AAA GAA        1668
His Ser Ser Arg His Ser Phe Asn Ile Arg His Arg Lys Gly
            485                 490                 495

AAT TAA TTA TGA AGCCTTTGGT TGTGACGTGT ACCCTTAAAG               1710
Asn

TTGGAACTTG TATGTTCTTA CTTGTAAATT GAATAATTAT                    1750

TTTTCTTAGG CAACTAAATT CTGCTCGTAT TGGAGTGGTG TTTGGTTGCC         1800

(2) INFORMATION FOR SEQ ID NO:2:

(i) SEQUENCE CHARACTERISTICS:
        (A) LENGTH:2601 base pairs
        (B) TYPE:Nucleic acid
        (C) STRANDEDNESS:Double
        (D) TOPOLOGY:Circular (ii) MOLECULE TYPE:Genomic DNA
        (A) DESCRIPTION:Partial genomic DNA sequence and deduced
            amino acid sequence of mucin binding protein (iii) HYPOTHETICAL:No (iv) ANTI-SENSE:Yes (v) FRAGMENT TYPE:N-terminal fragment (vi) ORIGINAL SOURCE:
        (A) ORGANISM:Lactobacillus reuteri sp
        (B) STRAIN:1063
        (C) CELL TYPE:Unicelluar organism (xi) SEQUENCE DESCRIPTION: SEQ ID NO:   2:

ATGATGTTCA ACAATTGGTT AAAGCTGCCA TTGAGTTAGG TGTCCAAATA         50

GACTTGCAAC CAACGCAAGT AGTATTATAT GTAGGAGATC ATCAAGAAAG         100

CTATAATGCT CAAGCAACTT TTGATTTCTC AAAGGGTGCT CGTGATGTAA         150
```

```
TTCTTAGTGA TTTTCCAGAA GTTCAGGATT TTCAGGAAAA GTAAAAAAGA            200

GACTGAGGAG ATTATTTCCT AGTCTCTATC TTTTTAAAGT AGGGTAATAA            250

CCTTGTTTTC ACTTTCGTTA TTTCCCGGGA AATAGAAAGA AGCGCTAAAA            300
```

| | | | | | | | | | | | | | | |
|---|---|---|---|---|---|---|---|---|---|---|---|---|---|---|
| ATG | AGA | AAG | ATT | GGA | ATT | GTT | GGC | CTC | GGT | CAT | GTG | GGT | GAA | 342 |
| Met | Arg | Lys | Ile | Gly | Ile | Val | Gly | Leu | Gly | His | Val | Gly | Glu | |
| 1 | | | | 5 | | | | | 10 | | | | | |
| ATG | CTA | GCC | AAC | CAA | TTA | GTA | ATG | AAC | GGA | AAA | GTT | GAT | GAA | 384 |
| Met | Leu | Ala | Asn | Gln | Leu | Val | Met | Asn | Gly | Lys | Val | Asp | Glu | |
| 15 | | | | | 20 | | | | | 25 | | | | |
| TTA | GTT | TTG | ATT | GAT | GAA | AAA | GAT | CCA | CAA | AAA | GGT | CAA | AAG | 426 |
| Leu | Val | Leu | Ile | Asp | Glu | Lys | Asp | Pro | Gln | Lys | Gly | Gln | Lys | |
| | 30 | | | | | 35 | | | | | 40 | | | |
| ACG | GTT | ACA | CAG | ACA | ATT | AAG | TAC | GAA | TAC | GCT | GAT | GGC | ACG | 468 |
| Thr | Val | Thr | Gln | Thr | Ile | Lys | Tyr | Glu | Tyr | Ala | Asp | Gly | Thr | |
| | | | 45 | | | | | 50 | | | | | 55 | |
| GCA | ACT | GGT | TTG | GCT | GAT | AAT | GTG | CAA | ACC | TTG | ACG | TTC | AAG | 510 |
| Ala | Thr | Gly | Leu | Ala | Asp | Asn | Val | Gln | Thr | Leu | Thr | Phe | Lys | |
| | | | | 60 | | | | | 65 | | | | | 70 |
| CGT | ACA | GGT | GAC | AAG | GAT | CTC | GTT | ACT | CAT | GAA | GTA | ACC | TGG | 552 |
| Arg | Thr | Gly | Asp | Lys | Asp | Leu | Val | Thr | His | Glu | Val | Thr | Trp | |
| | | | | | 75 | | | | | 80 | | | | |
| CCA | GAC | TGG | TCA | ACG | GTT | GCC | GGT | CAA | CAA | ACC | AGT | GTT | GTA | 594 |
| Pro | Asp | Trp | Ser | Thr | Val | Ala | Gly | Gln | Gln | Thr | Ser | Val | Val | |
| 85 | | | | | 90 | | | | | 95 | | | | |
| ACC | AGT | CCA | GCT | CTC | AAG | GGC | TAC | ACT | GCT | GAT | ACC | AAC | GAA | 636 |
| Thr | Ser | Pro | Ala | Leu | Lys | Gly | Tyr | Thr | Ala | Asp | Thr | Asn | Glu | |
| | | 100 | | | | | 105 | | | | | 110 | | |
| ATT | CCA | GCC | ATT | ACC | TAC | CAT | GCT | GGT | GAC | AGT | GAT | GTT | ACT | 678 |
| Ile | Pro | Ala | Ile | Thr | Tyr | His | Ala | Gly | Asp | Ser | Asp | Val | Thr | |
| | | | | 115 | | | | | 120 | | | | | 125 |
| TAT | GTT | GTT | AAG | TAC | AAT | GCC | GAT | GTT | CAA | CAT | GCT | GTT | ATC | 720 |
| Tyr | Val | Val | Lys | Tyr | Asn | Ala | Asp | Val | Gln | His | Ala | Val | Ile | |
| | | | | 130 | | | | | 135 | | | | | 140 |
| AAT | TAC | ATT | GAT | GGC | GAA | AGT | GAT | GAG | ATA | CTG | CAC | ACT | GAT | 762 |
| Asn | Tyr | Ile | Asp | Gly | Glu | Ser | Asp | Glu | Ile | Leu | His | Thr | Asp | |
| | | | | 145 | | | | | 150 | | | | | |
| AAG | GTT | AAT | GGC | CAC | TCT | GAC | GAA | AAG | ATC | AAC | TAC | AGC | ACT | 804 |
| Lys | Val | Asn | Gly | His | Ser | Asp | Glu | Lys | Ile | Asn | Tyr | Ser | Thr | |
| 155 | | | | | 160 | | | | | 165 | | | | |
| GCT | GAT | ATG | ATC | AAA | CAG | TTG | GAA | GCC | AAG | GGT | TAT | GAA | CTG | 846 |
| Ala | Asp | Met | Ile | Lys | Gln | Leu | Glu | Ala | Lys | Gly | Tyr | Glu | Leu | |
| | | 170 | | | | | 175 | | | | | 180 | | |
| TTC | AAG | GAC | AAC | TTC | CCA | GCT | GGT | GAG | AAG | TTC | GAT | AAC | GAT | 888 |
| Phe | Lys | Asp | Asn | Phe | Pro | Ala | Gly | Glu | Lys | Phe | Asp | Asn | Asp | |
| | | | | 185 | | | | | 190 | | | | | 195 |
| GAC | ACC | AAC | GAT | CAA | TTC | TAC | ACG | GTA | ATC | TTC | AAG | CAC | CAT | 930 |
| Asp | Thr | Asn | Asp | Gln | Phe | Tyr | Thr | Val | Ile | Phe | Lys | His | His | |
| | | | | | 200 | | | | | 205 | | | | 210 |
| CGT | GAA | AAC | GTT | GAT | CCA | AAC | CAC | TCC | TCG | GCT | GAT | GGC | ACG | 972 |
| Arg | Glu | Asn | Val | Asp | Pro | Asn | His | Ser | Ser | Ala | Asp | Gly | Thr | |
| | | | | | 215 | | | | | 220 | | | | |
| AAG | GGT | ACG | AAG | ACG | CTG | ACG | GAA | ACG | GTT | CAC | TAC | AAG | TAC | 1014 |
| Lys | Gly | Thr | Lys | Thr | Leu | Thr | Glu | Thr | Val | His | Tyr | Lys | Tyr | |
| 225 | | | | | 230 | | | | | 235 | | | | |
| GCT | AAT | GGC | ACC | AAG | GCG | GCT | GAA | GAT | CAG | ACG | GCT | CAG | GTA | 1056 |
| Ala | Asn | Gly | Thr | Lys | Ala | Ala | Glu | Asp | Gln | Thr | Ala | Gln | Val | |
| | | 240 | | | | | 245 | | | | | 250 | | |

```
ACG TTT ACG CGG AAC GGT GTC CTG GAT GAC GTT ACG GGT ATC         1098
Thr Phe Thr Arg Asn Gly Val Leu Asp Asp Val Thr Gly Ile
            255                 260                 265

GTG GCC TGG GGC AAG TGG AAC GAA GCC AGC CAG AGC TAC AAG         1140
Val Ala Trp Gly Lys Trp Asn Glu Ala Ser Gln Ser Tyr Lys
            270                 275                 280

GCT TTG ACT TCA CCA ACG ATT GCC GGC TAC GCG CCA AGC GAA         1182
Ala Leu Thr Ser Pro Thr Ile Ala Gly Tyr Ala Pro Ser Glu
                285                 290

GCG GTG GTA AAC CGC AGT TCC AAC AGC GAT GCC GAA CAA GGC         1224
Ala Val Val Asn Arg Ser Ser Asn Ser Asp Ala Glu Gln Gly
295                 300                 305

CCA ACG CTT ACC GTC ATT TAC ACG GCT GAT GCC CAA AAG GTT         1266
Pro Thr Leu Thr Val Ile Tyr Thr Ala Asp Ala Gln Lys Val
            310                 315                 320

CAC GTT CAA TAC ATT GAT GGT GAA ACT GAC CAG ATG CTG CGT         1308
His Val Gln Tyr Ile Asp Gly Alu Thr Asp Gln Met Leu Arg
            325                 330                 335

CAG GAT GAT TTG GAC GGC TAC ACG GAT GAA ACG ATT CCT TAC         1350
Gln Asp Asp Leu Asp Gly Tyr Thr Asp Glu Thr Ile Pro Tyr
            340                 345                 350

AGC ACG GCT GAA GGC ATC AAG AAG TTT GAA GGC GAC GGT TAT         1392
Ser Thr Ala Glu Gly Ile Lys Lys Phe Glu Gly Asp Gly Tyr
                355                 360

GAA CTG TTC AAG GAC AAC TTC CCA GCT GGT GAG AAG TTC GAT         1434
Glu Leu Phe Lys Asp Asn Phe Pro Ala Gly Glu Lys Phe Asp
365                 370                 375

AAC GAT GAC AAG AAT GAC CAA ACC TAC ACG GTA ATC TTC AAG         1476
Asn Asp Asp Lys Asn Asp Gln Thr Tyr Thr Val Ile Phe Lys
            380                 385                 390

CAC CAT CGT GAA AAC GTT GAT CCA AAC CAC TCC TCG GCT GAT         1518
His His Arg Glu Asn Val Asp Pro Asn His Ser Ser Arg Asp
            395                 400                 405

GGC ACG AAG GGT ACG AAG ACC CTG ACG GAA ACG GTT CAC TAC         1560
Gly Thr Lys Gly Thr Lys Thr Leu Thr Glu Thr Val His Tyr
            410                 415                 420

AAG TAC GCA GAT GGT ACC AAG GCC GCT GAA GAT CAG ACG GCT         1602
Lys Tyr Ala Asp Gly Thr Lys Ala Ala Glu Asp Gln Thr Ala
                425                 430

CAG GTA ACG TTT ACG CGG AAC GGT GTC CTG GAT GAC GTT ACG         1644
Gln Val Thr Phe Thr Arg Asn Gly Val Leu Asp Asp Val Thr
435                 440                 445

GGT ATC GTG GCC TGG GGC AAG TGG AAC GAA GCC AGC CAG AGC         1686
Gly Ile Val Ala Trp Gly Lys Trp Asn Glu Ala Ser Gln Ser
            450                 455                 460

TAC AAG GCT TTG ACT TCA CCA ACG ATT GCC GGC TAC ACG CCA         1728
Tyr Lys Arg Leu Thr Ser Pro Thr Ile Ala Gly Tyr Thr Pro
            465                 470                 475

AGC GAA GCG GTG GTA AAG CGC AGT TCC AAC AGC GAT GCC GAA         1770
Ser Glu Ala Val Val Lys Arg Ser Ser Asn Ser Asp Ala Glu
                480                 485                 490

CAA GGC CCA ACG CTT ACG GTC ATC TAC ACG GCT GAT GCC CAA         1812
Gln Gly Pro Thr Leu Thr Val Ile Tyr Thr Ala Asp Ala Gln
            495                 500

AAG GTT CAC GTT CAA TAC ATT GAT GGT GAA ACT GAC CAG ATG         1854
Lys Val His Val Gln Tyr Ile Asp Gly Glu Thr Asp Gln Met
505                 510                 515

CTG CGT CAG GAT GAT TTG GAC GGC TAC ACG GAT GAA ACG ATT         1896
Leu Arg Gln Asp Asp Leu Asp Gly Tyr Thr Asp Gly Thr Ile
            520                 525                 530
```

```
CCT TAC AGC ACG GCT GAA GGC ATC AAG AAG TTT GAA GGC GAC              1938
Pro Tyr Ser Thr Ala Glu Gly Ile Lys Lys Phe Glu Gly Asp
        535                 540                 545

GGT TAT GAA CTG TTC AAG GAC AAC TTC CCA GCT GGT GAG AAG              1980
Asp Tyr Glu Leu Phe Lys Asp Asn Phe Pro Ala Gly Glu Lys
            550                 555                 560

TTC GAT AAC GAT GAC ACC AAC GAT CAA TTC TAC ACG GTA ATC              2022
Phe Asp Asn Asp Asp Thr Asn Asp Gln Phe Tyr Thr Val Ile
                565                 570

TTC AAG CAC CAT CGT GAA AAC GTT GAT CCA AAC CAC TCC TCG              2064
Phe Lys His His Arg Glu Asn Val Asp Pro Asn His Ser Ser
575                 580                 585

GCT GAT GGC ACG AAG GGT ACG AAG ACG CTG ACG GAA ACG GTT              2106
Ala Asp Gly Thr Lys Gly Thr Lys Thr Leu Thr Glu Thr Val
        590                 595                 600

CAC TAC AAG TAC GCT AAT GGC ACC AAG GCG GCT GAA GAT CAG              2148
His Tyr Lys Tyr Ala Asn Gly Thr Lys Ala Ala Glu Asp Gln
            605                 610                 615

ACG GCT CAG GTA ACG TTT ACG CGG AAC GGT GTC CTG GAT GAC              2190
Thr Ala Gln Val Thr Phe Thr Arg Asn Gly Val Leu Asp Asp
                620                 625                 630

GTT ACG GGT ATC GTC GCC TGG GGC AAG TGG AAC GAA GCC AGC              2232
Val Thr Gly Ile Val Ala Trp Gly Lys Trp Asn Glu Ala Ser
        635                 640

CAG AGC TAC AAG GCT TTG ACT TCA CCA ACG ATT GCC GGC TAC              2274
Gln Ser Tyr Lys Ala Leu Thr Ser Pro Thr Ile Ala Gly Tyr
645                 650                 655

ACG CCA AGC GAA GCG GTG GTA AAG CGC AGT TCC AAC AGC GAT              2316
Thr Pro Ser Glu Ala Val Val Lys Arg Ser Ser Asn Ser Asp
        660                 665                 670

GCC GAA CAA GGC CCA ACG CTT ACG GTC ATC TAC ACG GCT GAT              2358
Ala Glu Gln Gly Pro Thr Leu Thr Val Ile Tyr Tht Ala Asp
            675                 680                 685

GCC CAA AAG GTT CAC GTT CAA TAC ATT GAT GGT GAA ACT GAC              2400
Ala Gln Lys Glu His Glu Gln Tyr Ile Asp Gly Glu Thr Asp
                690                 695                 700

CAG ATG CTG CGT CAG GAT GAT TTG GAC GGC TAC ACG GAT GAA              2442
Gln Met Leu Arg Gln Asp Asp Leu Asp Gly Tyr Thr Asp Glu
        705                 710

ACG ATT CCT TAC AGC ACG GCT GAA GGC ATC AAG AAG TTT GAA              2484
Thr Ile Pro Tyr Ser Thr Ala Glu Gly Ile Lys Lys Phe Glu
715                 720                 725

GGC GAC GGT TAT GAA CTG TTC AAG GAC AAC TTC CCA GCT GGT              2526
Gly Asp Gly Tyr Glu Leu Phe Lys Asp Asn Phe Pro Ala Gly
        730                 735                 740

GAG AAG TTC GAT AAC GAT GAC ACC AAC GAT CAT TCT ACA CGG              2568
Glu Lys Phe Asp Asn Asp Asp Thr Asn Asp His Ser Thr Arg
            745                 750                 755

TAT CTC AAG CCA CAT CGT GAA ACG TTG ATC CAA                          2601
Tyr Leu Lys Pro His Arg Glu Thr Leu Ile Gln
                760                 765
```

LACTOBACILLI HARBORING AGGREGATION GENE AS A VACCINE DELIVERY VEHICLE

FIELD OF THE INVENTION

This invention relates to the use of transformed Lactobacillus species and in a particular example, *Lactobacillus reuteri* (*L. reuteri*) as vaccine delivery vehicles. Transformed *L. reuteri* are demonstrated to express on their cell surface or to secrete an epitope of an antigen obtained from pathogenic microorganisms. In one embodiment, a gene (agg) encoding an aggregation protein and/or a gene (muc) encoding a mucin binding protein is fused to a gene encoding an exogenous antigen and used to transform Lactobacilli. The exogenous antigen attached to an aggregation protein or a mucin binding protein is expressed on the surface of the cell or secreted into its surroundings. Lactobacilli, and in particular *L. reuteri*, are highly effective in targeting the mucosa, such as the gastrointestinal tract or nasal passages, and when transformed as described herein, are effective in provoking a desired immune response against the presenting antigen in the host animal.

BACKGROUND OF THE INVENTION

Lactic acid bacteria have long been used as preservatives for food such as fermented milk, meat, fish, vegetables and cheese and in animal feed. Fermented foods are known to have beneficial effects on the human intestinal environment. Lactobacillus species are also useful as probiotics, microorganisms that have beneficial effects in the intestine and promote health when ingested.

Vaccines delivered orally are more convenient than the more commonly used parenteral delivery system, especially when vaccines are to be administered to large numbers of people or animals in less industrialized countries. Earlier attempts to develop oral vaccines have utilized pathogenic organisms, such as Salmonella species, as antigen carriers for oral immunization. However, even when these pathogens are attenuated they may pose a danger of reverting to pathogenicity and being harmful to the host animal. Lactic acid bacteria, in general, and Lactobacillus species in particular, possess certain properties that make them attractive candidates for use in oral vaccination. These properties of Lactobacillus include adjuvant activity, mucosal adhesive properties, and low intrinsic immunogenicity. They are generally regarded as safe (GRAS) as they are present in the animal's endogenous intestinal flora and are used commercially in the production of yogurts, cultured milks and other foods. Lactobacillus species are known to be difficult to transform with new genetic information. Those unable to be transformed are referred to as recalcitrants.

The gastrointestinal tract of animals is a complex ecosystem harboring an estimated 300 to 500 species of microorganisms. Despite over 100 years of intensive research in the field of intestinal microbiology, much remains to be learned about these microorganisms. Complex inter-relationships exist among different species of microorganisms and between resident microorganisms and their hosts.

An important factor concerning the utility of Lactobacillus species as a vaccine delivery vehicle is their ability to adhere to the epithelial cells of the animal to be vaccinated. Knowledge of the structure and mode of expression of surface related proteins of Lactobacillus that are involved in adherence to mucosal tissues and/or the extra-cellular matrix is important in designing an effective vaccination system. Adherence factors can be critical to proper antigen presentation in order for recombinant strains of lactic acid bacteria to elicit mucosal IgA and/or serum IgG responses to the expressed antigen in a host.

Lactobacilli are Gram-positive, non-sporeforming rods. They are important members of the normal human oral, gastrointestinal, and genital flora and are non-pathogenic to humans and animals. Lactobacilli including *L. reuteri* have been found in the gastrointestinal tract of all mammals studied to this time (Mitsuoka, 1992) including humans, pigs, chickens, cattle, dogs, mice, rats and hamsters. The ubiquity of Lactobacillus species in the mammalian gastrointestinal tract combined with their ability to target and adhere to mucosal receptors make them useful organisms as vectors for vaccinating a host against a wide range of pathogens.

Although many infectious agents gain access to the body by colonizing mucosal surfaces, very few infections caused by these agents have been effectively prevented by using mucosal, i.e., oral immunization (Wells et al, "Lactic acid bacteria as vaccine delivery vehicles", *Antonie van Leeuwenhoek* 70:317, Kluwer Academic Publishers, 1996). Oral immunization is highly desirable because of ease and the low cost of vaccine delivery, storage and administration. An effective delivery vehicle or organism should be one that is normally present in the gastrointestinal tract of the host organism and must accurately target the mucosal sites of infection and adhere to the mucosal surface. Lactobacilli possess both of these characteristics. A useful vaccine delivery vehicle must, in addition, be capable of expressing antigens of interest at sufficiently high levels to successfully immunize the host and must be non-pathogenic to the host.

Previous work on oral vaccination has focused on the development of modified pathogenic bacteria as antigen delivery vehicles (Stocker, U.S. Patent No. 4,837,151, Auxotrophic Mutants of Several Strains of Salmonella; Clements et al., U.S. Pat. No. 5,079,165, Avirulent Strains of Salmonella; Charles et al., U.S. Pat. No. 5,547,664, Live-attenuated Salmonella). The efficacy of these bacteria as vaccines is thought to depend on their invasiveness, capacity to survive and multiply, and on adequate levels of antigen gene expression in vivo. It is unclear, however, whether pathogenic strains that are sufficiently attenuated to pose no danger to recipients will retain their ability to invade target areas, multiply, and express adequate antigen levels (Wells et al.). This has led the present inventors to investigate the use of lactic acid bacteria, Lactobacilli and particularly *L. reuteri*, that have been modified to express exogenous antigens.

Leer et al. (WO095/35389) disclose a method for introducing nucleic acid into microorganisms, including microorganisms such as Lactobacillus and Bifidobacterium species that are difficult to transform or transfect. The method of Leer et al. is based on limited autolysis before the transformation process is undertaken.

Published PCT application PCT/NL96/00409 describes methods for screening non-pathogenic bacteria, in particular lactic acid bacteria of the genera Lactobacillus and Bifidobacterium, for the ability to adhere to specific mucosal receptors. The method comprises screening for adherence factors found on these non-pathogenic bacteria that are structurally related to virulence factors of some pathogenic microorganisms. An expression vector is also disclosed that comprises an expression promoter sequence, a nucleic acid sequence, and sequences permitting ribosome recognition and translation capability. This reference indicates that various strains of Lactobacillus can be transformed so as to express heterologous gene products including proteins of pathogenic bacteria.

Oral administration of recombinant L. lactis has been used to elicit local IgA and/or serum IgG antibody responses to an expressed antigen (Wells et al.). This indicates that in L. lactis, expressed heterologous proteins may elicit antigenic responses in a host organism. However, this reference and none of the prior art teaches that L. reuteri, a species with particularly desirable indigenous characteristics of mucosal targeting and adherence, can be transformed with heterologous DNA and express the foreign protein on the surface of the L. reuteri cell or secreted by the cell. The prior art fails to suggest or disclose the transformation of Lactobacillus with the aggregating gene agg or the mucin binding gene muc as set forth below.

U.S. Patent No. 5,413,960 to Dobrogosz teaches a method for obtaining the antibiotic β-hydroxyproprionaldehyde, or reuterin, which is active against both Gram- positive and Gram-negative bacteria by culturing L. reuteri under anaerobic conditions in the presence of glycerol or glyceraldehyde. U.S. Pat. No. 5,352,586 also to Dobrogosz describes a method of identifying strains of L. reuteri that produce the antibiotic reuterin. In both patents the antibiotic producing L. reuteri strains are identified by their ability to inhibit the growth of susceptible microorganisms in the presence of glycerol or glyceraldehyde. These references provide a method for obtaining strains of L. reuteri that secrete the antibiotic reuterin useful in the treatment of infection caused by various pathogenic microorganisms.

U.S. Pat. No. 5,439,678 claims a method for providing a probiotic to an animal which comprises feeding the animals L. reuteri. The term "probiotic" refers to ingested microorganisms that can live in a host and contribute positively to the host's health and well-being. The teachings of U.S. Pat. Nos. 5,352,586, 5,439,678 and 5,413,960 are incorporated herein by reference. These patents, however, do not suggest or disclose the use of L. reuteri as a vaccine delivery vehicle.

Heng, N.C.K. et al. (Cloning and Expression of an Endo-1,3-1,4-β-Glucanase Gene from *Bacillus macerans* in *Lactobacillus reuteri*, Appl. and Environ. Microbiol, 3336–3340, Aug. 1997) describe the cloning, expression, and secretion of a heterologous gene derived from another bacterial species in a strain of L. reuteri that originated in the gastrointestinal tract. The authors believe this to be the first demonstration of the expression of a gene of heterologous origin in L. reuteri. Heng et al. were also able to demonstrate secretion by L. reuteri of the gene product, β-glucanase, indicating that the heterologous secretion signals were recognized by the L. reuteri cells.

SUMMARY OF THE INVENTION

In its broadest aspect, this invention discloses a method for vaccinating an animal by administering to said animal a recombinant Lactobacilli that have been transformed to express exogenous antigens. A particular example uses recombinant L. reuteri as the vaccine delivery vehicle which has been modified to express an epitope derived from enterotoxigenic *Escherichia coli* (*E. coli*) or enteropathogenic *E. coli*. One aspect of the invention relates to the discovery of genes responsible for the production of proteins that provide for the aggregation of individual cells and binding to mucin. The sequence for a gene (agg) that facilitates adhesion by controlling aggregation in Lactobacillus species is disclosed. The partial sequence for a gene (muc) that enhances binding to mucin is also disclosed.

Mucin is any of various mucoproteins that occur in the secretions of mucous membranes. The mucous membranes are rich in mucous glands which line an animal's body passages and cavities which communicate directly or indirectly with the exterior. Mucus is the viscid, slippery secretion that is usually rich in mucins and is produced by mucous membranes which it moistens and protects. Representative of the mucous membrane containing tissues which the vaccines of the present invention are effective in preventing or treating infections include the nasopharynx (nasal passages), pharynx, esophagus, stomach, small intestine and large intestine.

A method is provided for transforming Lactobacilli with the genetic information for an exogenous epitope derived from a pathogenic organism combined with additional copies of a Lactobacillus agg and/or muc gene and expressing the encoded proteins either on the cell surface or secreting the proteins from the cell. The recombinant Lactobacilli expressing agg and an exogenous antigen and/or muc and an exogenous antigen are then used as a vaccine to provide protection against disease caused by the donor pathogen. Examples of the method are provided using L. reuteri.

The invention further relates to recombinant Lactobacillus species that are capable of consistently and accurately reaching and adhering to target locations on the mucosa of the host and expressing there heterologous antigenic proteins derived from pathogenic organisms or from other biological material.

*E. coli* are Gram negative, non-sporeforming rods that are present in large numbers in the gastrointestinal tract of humans and animals. Some strains of *E. coli* cause gastroenteritis mediated by heat-labile and heat-stable enterotoxins comprising both endotoxins that are integral parts of the cell wall and exotoxins that are secreted by the bacterial cell. Secreted toxin is adsorbed to gangliosides at the brush border of epithelial cells of the small intestine. The genes for both types of toxins are located on plasmids. The plasmids carrying the genes for enterotoxins also carry genes that direct the synthesis of specific surface antigens that are essential for the attachment of E. coli to intestinal epithelial cells, such as one known as K88 isolated from piglet *E. coli*. Nucleic acid probes have been used to detect toxin genes. Maximum virulence is associated with specific adhesive fimbriae, hairlike projections on the bacterial cell surface. The primary function of fimbriae is to mediate adherence of the bacterial cell to other bacteria, to mammalian cells, or to hard and soft surfaces. This is an important feature in the pathogenesis of such microorganisms.

Both gastroenteritis produced by enterotoxigenic *E. coli* and childhood diarrhea caused by enteropathogenic strains of *E. coli* are mostly observed in underdeveloped countries. A safe and effective vaccine, would be extremely beneficial in preventing and treating disease caused by these organisms.

An additional aspect of the invention comprises the use of recombinant DNA technology to prepare expression vectors comprising genes encoding cellular aggregation (agg) and/or enhanced binding to mucin (muc) and DNA encoding an antigenic virulence factor obtained from a pathogenic microorganism, inserting the expression vectors into cells of a Lactobacillus species, and selecting transformed cells expressing the complete or partial heterologous protein at high levels. The invention further discloses the administration of such transformed Lactobacillus cells to an animal to provoke an immune response in the animal at a level and for a duration that will effectively vaccinate the animal against infection by the pathogenic microorganisms. The present invention optionally provides for the administration of antibiotics to the recipient mammal subsequent to administration of the transformed microorganism in order to eradicate the transformed microorganism from the vaccinated host.

Methods for preparing live vaccines from transformed strains of Lactobacillus species are also disclosed. The vaccines will be useful for vaccinating an animal host susceptible to disease from various pathogenic microorganisms, such as bacteria and viruses and also to create a desired immunological response to other biological materials. Transformed Lactobacilli serve as carriers for antigens so as to produce an immunologic response in the host. Transformed Lactobacilli can thereby serve as vaccine delivery systems to an animal in need of vaccination. The heterologous antigens expressed on the surface or secreted into the surroundings of the Lactobacilli will provide protection to the host.

A strain of L. reuteri is also provided which expresses an antigen of a pathogenic microorganism as a result of introducing into the L. reuteri cells an expression cassette comprising DNA sequences encoding the antigen under control of regulatory regions recognized by the L. reuteri cells.

There is further disclosed a method for vaccinating an animal with a live, non-virulent vaccine comprising the steps of: (a) identifying and selecting strains of non-pathogenic microorganisms such as Lactobacilli displaying desirable characteristics for targeting and adhering to mucosal tissue; (b) identifying and selecting those strains of non-pathogenic microorganisms such as Lactobacilli additionally demonstrating the potential to express foreign proteins; (c) identifying and isolating the gene or genes encoding antigenic proteins from a pathogenic microorganism or other biological material; (d) inserting the genes of step (c) into an appropriate expression cassette or construct containing regulatory regions recognized by a host microorganism identified in steps (a) and (b) and the genes agg and/or muc; (e) transferring the expression cassette into cells of the host microorganism to form a transformed organism; (f) selecting and growing the transformed cells that can express antigenic proteins encoded by the inserted gene sequences on their cell surface; and (g) combining the modified cells with pharmaceutically acceptable carriers and excipients to form a vaccine for oral, nasal or other direct delivery to mucosal surfaces. An additional step in the disclosed method is to use antibiotics to eradicate the transformed microorganisms after colonization.

Another aspect of the invention relates to the isolation, sequencing and expression of a gene, agg, identified in Lactobacilli that regulates the ability of the cells to aggregate in situ. Also disclosed is the isolation and partial sequencing of a gene, muc, and its expressed protein that increases the ability of a microorganism to adhere to the mucosa of an animal.

DETAILED DESCRIPTION OF THE INVENTION

As used herein and in the claims, the term "animal" means mammals and avians, with humans being the animal of greatest interest. As used herein and in the claims, the term "L. reuteri" means any Lactobacillus microorganism that is identified as L. reuteri according to the method set forth in U.S. Pat. No. 5,352,586. As used herein and in the claims, the terms "transformed Lactobacilli or "transformed L. reuteri" mean Lactobacilli or L. reuteri into which foreign genes encoding antigenic products have been inserted. Transformed L. reuteri, or other similarly transformed bacteria particularly other Lactobacillus species, may be administered in the form of a capsule, tablet, yogurt, solution or the like. Adequate dosages to establish transformed bacteria in the normal flora of an animal to effectuate vaccination is within the skill of the artisan. All embodiments of the invention require the use of viable transformed non-virulent bacteria, preferably Lactobacilli and more preferably L. reuteri, as the organism which provides for the production of antigenic products in the animal body at sites that elicit an immune response.

Vaccines according to the invention are prepared from live bacteria preferably Lactobacilli, and more preferably L. reuteri, that have been transformed so as to express antigens of microorganisms pathogenic to the host. The transformed bacteria, which serve as hosts for the expression of the antigen, can express the antigen in the cytoplasm which can then be translocated to the outer membrane of the microorganism or secreted to provide immunogens for an immunologic response by the animal host. By employing live, non-virulent bacteria as carriers for an immunogen, a strong targeted stimulus can be provided to the immune system. The antigen gene which is inserted into the host non-virulent bacteria may come from diverse sources, such as pathogenic bacteria, viruses, fungi, protozoa, or other biological material.

The antigen gene may encode envelope proteins, capsid proteins, surface proteins or toxins such as exotoxins or enterotoxins. The antigen gene may also specify enzymes or other proteins needed for the synthesis of a polysaccharide or an oligosaccharide. The antigen genes are isolated in conventional ways employing probes where at least a partial amino acid or nucleic acid sequence is known. Representative of the antigen genes useful in transforming the Lactobacilli include those specifying the enterotoxins of enterotoxigenic or enteropathogenic E. coli or Vibrio cholerae strains; the HBsAg, surface, envelope or capsid proteins of T. cruzi, B. pertussis, Streptococci, Haemophilus, Neisseria, Pseudomonas, Pasteurella, Chlamydia, Adenovrus, Astrovirus, herpes virus, myxovirus, retrovirus, rotavirus and the like. The antigen gene may also specify an enzyme needed for synthesis of polysaccharides, e.g., Meningococcus capsular polysaccharide, or for the modification of an oligosaccharide or polysaccharide of the host microorganism. The preceding list is exemplary and not a comprehensive list of the possible sources of genetic information that may be transferred by the methods disclosed.

As an example, strains of L. reuteri that consistently and accurately target and adhere to mucosal surfaces, thereby demonstrating potential usefulness as a vehicle for the presentation of foreign antigens to the mucosa, are selected for transformation. Genes or DNA sequences encoding a heterologous antigen and, if desired, other genetic information are introduced into L. reuteri using molecular biology techniques known in the art.

Lactobacillus reuteri (L. reuteri), is a recently designated species of Lactobacillus. Some strains of this species were previously identified as Lactobacillus fermentum. L. reuteri is a symbiotic resident of the gastrointestinal tracts of humans, swine and other animals. The neotype strain of L. reuteri is DSM20016 (ATCC No. 53609). This strain and other strains including L. reuteri 1063 (ATCC No. 53608) are available to the public at the American Type Culture Collection 10801 University Boulevard, Manassas, Va. 20110-2209 having been deposited therein under the Budapest Treaty of Apr. 17, 1987.

Some Lactobacillus species are known as recalcitrants as they are difficult to transform using known techniques.

Various methods of transforming L. reuteri have been disclosed. One method for transforming L. reuteri is described in an International Application published under the Patent Cooperation Treaty, PCT 95/NL00215 (WO95/35389) to Leer et al. which is incorporated herein by reference. The method of Leer et al. requires subjecting L. reuteri to limited autolysis during or before the transformation process. Limited autolysis is carried out by incubating the microorganism in a low molarity electroporation buffer containing an osmotic stabilizer, generally at a pH of between 4 and 8 and at a temperature below 37° C., more preferably between 0 and 10° C.

A method for the construction of multi-purpose plasmid vectors and expression vectors for lactic acid bacteria is disclosed in PCT/NL95/9135 to Nederlandse Organisatie voor Toegpast Natuurwetenschappelijk Onderzoek (TNO). This method can be used to construct vectors that can be used for the introduction, stable maintenance, and efficient expression of foreign genes in lactic acid bacterial species including Lactobacilli. Modification of this method enables Lactobacilli to express, secrete, and display heterologous antigens on the cell surface and thereby function as an effective vaccine in its target location. The expression vector disclosed in the instant application comprises an expression promoter sequence controlling a nucleic acid sequence encoding a heterologous antigenic protein or polypeptide or alternatively additional copies of a native Lactobacillus gene, such as agg or muc, whose expression it is desired to augment. The encoding nucleic acid sequence is preceded by a 5' non-translated nucleic acid sequence comprising the minimal sequence required for ribosome recognition and RNA stabilization, followed by a translation initiation codon.

It is important that strains selected for transformation not only have the ability to express inserted genes encoding foreign protein they must also, in order to be effective as vaccine delivery vehicles, adhere efficiently to target mucous membranes. Therefore, Lactobacilli cells were selected that express adhesion factors efficiently.

The protocol for developing strains of Lactobacilli, in particular strains of L. reuteri, with improved adhesion factors comprises the following steps:

(1) isolating and characterizing genes involved in the synthesis and secretion of adhesion factors in Lactobacilli;

(2) selecting or constructing strains containing genes resulting in adhesion factors with improved properties; and (3) demonstrating the capacity of strains with improved adhesion factors to displace and thereby interfere with adhesion of pathogenic bacteria to mucosal receptors.

The protocol for preparing a vaccine according to the present invention comprises the following steps:

(1) identifying and selecting strains of Lactobacilli displaying desirable characteristics for targeting and adhering to mucosal tissue efficiently;

(2) identifying and selecting strains of Lactobacilli additionally demonstrating the potential to express heterologous proteins;

(3) identifying and isolating the gene or genes encoding antigenic proteins of interest in a pathogenic microorganism or in other biological material;

(4) fusing the genes of step (3) with a gene agg encoding information for bacterial aggregation and/or a gene muc encoding information for bacterial binding to mucins;

(5) inserting the fused genes into an appropriate expression vector containing regulatory regions recognized by Lactobacilli;

(6) transferring the expression vector into the selected Lactobacillus cells;

(7) selecting and growing transformed Lactobacillus cells that can replicate and express antigenic determinants encoded by the inserted gene sequences on the cell surface;

(8) combining the transformed Lactobacilli with pharmaceutical carriers to form vaccine for oral, nasal or other direct delivery to mucosal tissue; and (9) administering the vaccine to a human or other animal recipient.

EXAMPLE I

Enhancement of Aggregation

The ability to form multicellular aggregates has been reported for a number of bacterial species. This phenomenon is described either as autoaggregation, involving bacteria from the same strain, or as coaggregation where different bacterial strains are involved. Both types of aggregation have been described in Lactobacillus species. It has been suggested that autoaggregation and coaggregation are important for the ability of the bacteria to colonize and thereby effect the removal of intestinal pathogens. In Lactobacilli, there is a demonstrated connection between aggregation and genetic exchange. It has been reported that a 32 kD aggregation promotion factor in L. plantarum is immunologically crossreactive with a protein of similar size that mediates aggregation in Lactobacilli.

This experiment is directed to a cloned and sequenced gene from L. reuteri that encodes a 60 kD protein that mediates aggregation. Introduction of additional copies of the gene into an L. reuteri strain markedly enhanced aggregation behavior. The sequenced gene was found to have extensive sequence homology to a large family of ATP-dependent RNA helicases. It was demonstrated in this work and disclosed herein that autoaggregation by L. reuteri involves the activity of a protein with extensive homology to RNA helicases.

MATERIALS AND METHODS

Bacterial Strains and Growth Conditions

In this experiment, a strain of Lactobacilli known as L. reuteri 1063 was used to isolate the gene for a 60 kD protein which demonstrates aggregating activity in vitro and in vivo. L reuteri strains 1063 and 1068 were previously isolated from the small intestine of a pig. L. reuteri DSM 20016 was obtained from the "Deutsche Sammlung von Mikroorganismen", Gottingen, Germany. E. coli LE392 was used as lambda (λ) host strain and E. coli TG1 as host strain in subcloning and expression of the recombinant protein. L. reuteri were grown on Man-Rogosa-Sharpe (MRS) agar or in MRS broth (Oxoid Ltd., Basingstoke, England). Plates were incubated in anaerobic jars under $CO_2$ and $N_2$ atmosphere (GasPak System, BBL, Cockeysville, Md., USA) at 37° C. E. coli broth cultures were grown at 37° C. in Luria-Bertani (LB) broth on a rotary shaker or on LB agar. When antibiotics were used for selection, the concentrations were: 50 μ/ml Ampicillin (Amp) and 8 μ/ml Chloramphenicol (Cm) for both E. coli and Lactobacilli.

Proteins and Reagents

L. reuteri strain 1063 was grown in 500 ml MRS broth and the cells were harvested by centrifugation at 10,000 ×g.

The spent culture medium was dialysed and subsequently lyophilized. The bacteria were washed repeatedly with 500 ml portions of distilled water until the autoaggregating activity was lost. The wash solutions were also dialysed and lyophilized. Antiserum against a mix of the high molecular weight (MW) fractions from the spent growth medium and the wash solutions were raised in a rabbit. The rabbit was immunized with the proteins and given three booster doses in two week intervals. The animal was sacrificed eight weeks after the first immunization.

In order to make the antiserum more specific against the aggregation factor, it was adsorbed against the nonaggregating L. reuteri strain 1068. The bacteria were grown in 200 ml MRS for 16 hours and washed twice in phosphate-buffered saline (PBS) at pH 7.3 supplemented with 0.05% Tween 20 (PBST). The cells were then suspended in 20 ml PBST. One ml of antiserum was mixed with 1 ml of bacterial suspension and incubated at room temperature for two hours. After centrifugation the adsorbed antiserum were sterile filtered through a 0.2 μm filter. The IgG-fraction from the adsorbed antiserum was purified on ProteinA-Sepharose (Pharmacia, Uppsala, Sweden) according to the manufacturer's instructions.

Construction and Screening of a λ-Library

L. reuteri strain 1063 was grown in 100 ml MRS broth and DNA was extracted according to Axelsson and Lindgren (1987). The DNA was partially digested with Sau3A and ligated into Lambda EMBL3 BamHI arms. Packaging into phage particles was performed according to the manufacturer's instructions (Promega, Madison, Wis., USA). After infection of E. coli LE392, the resulting plaques were screened with the IgG-fraction from the antiserum (Roos et al., FEMS, Microbiology Letters, 144:33–38,1996).

Affinity Purification of Recombinant Protein

The IgG-fraction of the antiserum was coupled to CnBr-activated Sepharose (Pharmacia) according to the manufacturer's instructions. Positive λ-clones from the screening procedure were used to produce large scale λ-lysates (Maniatis et al., Molecular Cloning, A Laboratory Manual, 1982). The lysates were centrifuged and applied to the Sepharose coupled with the Ig-G fraction. The column was washed with PBS until $A_{280}$ of the collected fractions had reached the baseline. The adsorbed proteins were eluted with 1 M HAc. After neutralization with 1 M Tris-Base the eluted proteins were dialysed twice against a large volume of distilled water. The protein material was then lyophilized and dissolved in PBS.

AGGREGATION ASSAY

The affinity purified protein from the different classes of recombinants was examined for the ability to aggregate L. reuteri in vitro. L. reuteri 1063 was grown in 10 ml MRS for sixteen hours. The bacteria were washed five times with 10 ml of distilled water which resulted in a loss of aggregation. The bacteria were suspended in 1 ml of distilled water and 10 μl of bacterial suspension was mixed with 1 μl of affinity purified protein on a microscopy slide glass. Occurrence of aggregates within one minute was recorded as a positive test.

Subcloning and Isolation of Positive Clones

DNA from λ-clone 105:2 was isolated and cleaved in separate reactions with EcoRI, HindIII, PstI, SalI and ScaI. The material from the different cleavages were pooled, treated with T4 DNA polymerase in order to generate blunt ends, and then ligated into a SmaI cleaved pUC 18 vector. The ligation mix was electroporated into E. coli TG1 cells and the resulting clones were selected on LA plates supplemented with Amp and screened with the IgG-fraction from the antiserum. Plasmids from positive clones were purified with Wizard Minipreps DNA purification system (Promega) and characterized with restriction enzyme analyses and sequencing.

Introduction of the Agg Gene into L. reuteri Strains

A broad host range vector, pVS2, (von Wright et al., Applied Environ. Microbiol 53:1584–1588, 1987) harboring a chloramphenicol resistance gene was cleaved with HindIII and blunt ends were generated by treatment with T4 DNA polymerase. A 2450 bp BglII fragment of chromosomal DNA was also treated with T4 DNA polymerase and thereafter ligated at the single Cla1 site into pVS2. This construct is called pAGG1. The ligation mix was electroporated into E. coli TG1 cells and transformants were selected on plates with chloramphenicol (Cm) and screened with the IgG-fraction. The plasmid from one positive clone was electroporated into L. reuteri DSM 20016 and strain 1068 according to the method of Ahrne et al., (Current Microbiology 24: 199–205), and transformants were selected on MRS plates with chloramphenicol. In order to detect an in vivo effect of the gene, the resulting clones were grown in 10 ml MRS supplemented with Cm for 16 hours at 37° C.

DNA Sequencing and Analysis of the Sequence

Sequencing was performed by the dideoxy method, using ABI PRISM Dye Terminator Cycle Sequencing Ready Reaction Kit (Perkin-Elmer, Foster City, Calif., USA) with commercial standard and customized sequencing primers. The sequencing samples were analyzed on the automatic sequencing machine ABI 373 (Perkin-Elmer). The PC/GENE DNA and protein data handling package was used for analysis of the DNA and deduced protein sequence.

SDS-PAGE and Western Blotting

SDS-PAGE and Western blot analyses were performed with the PhastSystem (Pharmacia) according to the manufacturer's instructions and the proteins were blotted to a Protran BA85 nitrocellulose membrane (Schleicher and Schüell, Dassel, Germany) by diffusion at 65° C. for 45 minutes. Blocking of the membranes, incubations with the IgG-fraction and HRP-conjugated secondary antibody was performed according to Roos et al., 1996. The membranes were finally developed with 4-chloro-1-naphtol as substrate.

Results

The agg gene of L. reuteri strain 1063 was cloned and found to reside on a 2450 bp chromosomal BglII fragment. As described above, antiserum was raised against extracellular and cell surface proteins from L. reuteri strain 1063 and was used to screen a λ-library generated from the same strain. A large number of clones were identified that were reactive with the antiserum. Further examination of the recombinant proteins expressed by these clones showed that they represented three different classes as judged by band pattern in Western blot analyses. Representatives from the different classes of clones were used to produce recombinant protein which was subsequently affinity purified on the immobilized IgG-fraction of the same antisera that was used in the initial screening. One class of clones expressed a 60 kD protein that promoted aggregation in a glass slide experiment. Subcloning of the DNA from one of these clones, λ105:2, into a plasmid vector allowed identification of clones reacting with the antisera and expressing a protein band of the same size as the λ-clone. One of these clones, designated LrAg7, was harboring a 3.4 kb HindIII fragment. Further deletions and subclonings allowed the identification of a 2450 bp chromosomal BglII fragment encoding the responsible protein.

Sequence analysis of the BglII fragment revealed an open reading frame of 1491 nucleotides (nt) coding for a polypeptide containing 497 amino acids with a predicted molecular mass of 56 kD. The initiation codon TTG is preceded by a ribosome binding site, and further upstream, by possible transcription initiation signals. The deduced amino acid sequence was used for homology searches in the data banks and extensive sequence similarity to the large family of DEAD-box helicases was found. The best match was with a *Bacillus subtilis* protein that is a proposed ATP-dependent RNA helicase. Nucleotide and amino acid sequences for the agg gene are provided as directed in 37 C.F.R.§1.821 through §1.825 and are identified as SEQ ID No: 1 in the Sequence Listing.

In order to establish that the agg gene is actually encoding a protein with aggregating effect in vivo, the BglII fragment was cloned into the broad host range vector pVS2 and the construct was introduced into *L. reuteri*. The gene was introduced into *L. reuteri* 1063, which has an aggregating phenotype. The transformed microorganisms exhibited markedly enhanced aggregation compared with the native microorganism.

EXAMPLE II

Use Of The Agg Gene In A Gene Fusion System For Expression

And Secretion of Fused Proteins

Using recombinant DNA techniques, as described in Example I, expression vectors containing heterologous genes of interest are prepared and inserted into Lactobacillus cells that have demonstrated capability for expressing a protein encoded by inserted genes.

Fusion of the agg gene to the gene for K88ab fimbriae:

The agg gene of *L. reuteri* strain 1063 was cloned and defined to reside on a 2450 bp chromosomal BglII fragment as described in Example I. This BglII fragment of chromosomal DNA was cloned at the single ClaI site of the plasmid vector pVS2 (von Wright et al., 1987). Before ligation the chromosomal fragment and the vector were treated with T4 DNA polymerase to create blunt ends (Maniatis et al., 1982). This construct, pAGG1, was cleaved at position 1622 with Cla1 to generate a linear molecule.

The gene encoding the K88ab fimbriae of *E. coli* was identified by Gaastra, W. et al., (The nucleotide sequence of the gene encoding the K88ab protein subunit of porcine entertoxic *Escherichia coli*. FEMS MicrobioL. Lett. 12: 41–46, 1981); and characterized by Bakker et al., (Characterization of the antigenic and adhesive properties of FaeG, the major subunit of K88 fimbriae. *Mol. Microbiol.* 6 (2): 247–255, 1992). PCR was used to identify a suitably useful fragment of the K88ab gene. PCR primers used were as follows:

5'-AAATCGATGCCTGGATGACTGGTGAT-3'; and
5'-AAATCGATTAGGCAGCAGAAACAACAGT-3'.

Standard PCR procedures (Ehrlich, H. A. and Arnheim, N., *Annu Rev. Genet.*26: 479–506, 1992) are followed to obtain a 705 bp product. The product of PCR is cleaved with ClaI and ligated into ClaI cleaved pAGG1. The resulting construct is electrotransformed into *E. coli* TG 1 cells and the resulting transformants analyzed to identify clones containing the fused genes. An identified clone is verified by sequencing and denoted as pKAGG1.

Introduction of the fusion gene construct pKAGG1 into *L. reuteri*

The construct pKAGG1, expressing a fusion protein consisting of part of the AGG protein from *L. reuteri* and part of the K88ab fimbriae of *E. coli* is electrotransformed into *L. reuteri* strains 1063 and 1068 using the method of Ahrne et al., (Ahrne, S., Molin, G., and Axelsson, L. Transformation of *Lactobacillus reuteri* with electroporation: Studies on the erythromycin resistance plasmid pLUL631. *Current Microbiol. Vol* 24, 199–205, 1992). Transformants are isolated on agar plates containing 10 mcg/ml erythromycin. The production of fusion protein is detected by using antibodies against either the AGG protein and/or antibodies against the K88ab fimbriae.

Using the methodology of the present invention genes encoding enterotoxins secreted by enterotoxigenic or enteropathogenic strains of *E. coli* are fused to the agg gene of *L. reuteri* and inserted into an expression cassette having an appropriate promoter sequence and other regulatory regions recognized by *L. reuteri* cells. The cassette is then transferred into *L. reuteri* cells that have been determined to be capable of expressing inserted genes. Cells that have been successfully transformed and express the inserted genes, as indicated by the presence of *E. coli* antigens on the cell surface are selected for immunologic evaluation. *L. reuteri* cells expressing *E. coli* antigens are placed in a suitable pharmaceutical carrier or food product such as milk or yogurt and delivered as a vaccine to mammals susceptible to infection by toxic strains of *E. coli*. Vaccinated and unvaccinated mammals are challenged with live enterotoxigenic *E. Coli* (ETEC) and evaluated for subsequent infection in order to determine whether the antigen expressing Lactobacilli conferred protective immunity.

The described procedure can be used with a wide variety of pathogenic organisms for which genes for antigenic factors are available by transferring appropriate genes into competent *L. reuteri* or other Lactobacilli that have either the agg gene or a homologous gene. Lactobacilli, particularly *L. reuteri*, are the preferred hosts for the plasmid containing the fused genes, however, the procedure can be used to transform other bacterial species. The procedure can also be modified so that the fused genes can be inserted directly into the host chromosome instead of being introduced on a plasmid vector.

EXAMPLE III

Use Of The Agg Gene In A Gene Fusion System That Is Integrated Into The

Chromosome Of A Recipient Cell

Using recombinant DNA techniques described in Examples I and II, expression vectors containing heterologous genes of interest and prepared, inserted into *L. reuteri* cells and integrated into the chromosome of the cell.

The agg gene and the K88 gene of *E. coli* described in Examples I and II were cloned into a temperature sensitive shuttle vector, pJRS233, whose construction is described in Perez-Casal et al. (*Molec. Microbiol*.8(5):809–819, 1993). The vector pJRS233 was generated from a temperature sensitive plasmid demonstrated by Maguin et al. (New Thermosensitive Plasmid for Gram-Positive Bacteria, *J Bacteriol.* 174:5633–5638, 1992) to be stable at temperatures below 35° C. in lactic acid bacteria. The Cla I site in pJRS233 was initially cleaved with ClaI, thereby destroying the site, then treated with T4 polymerase, and religated. The BglII fragment with the agg gene, described in Example I, was cloned into the BamHI site of modified pJRS233 and the PCR fragment from the K88 gene, described in Example II, was cloned into the Cla1 site. The resulting construct containing both the agg and K88 genes is called pAGGts1.

Plasmid pAGGts1 was electrotransformed into *L. reuteri* 1063. Integration of the plasmid into the chromosome of *L reuteri* was accomplished by a modification of the method of Bhowmik et al. (*J Bact., pp.* 6341–6344, Oct. 1993). The construct pAGGts1 is a temperature sensitive integration plasmid that can be introduced and propagated in Lactobacillus species, including *L. reuteri*. After introduction of the plasmid, the bacteria were propagated at 46° C., a non-permissive temperature, in order to turn off replication of the plasmid and select for clones in which the construct had been inserted into the chromosome. Clones in which the native gene and the vector have been deleted were isolated as described in Bhowmik et al.

EXAMPLE IV

Identification Of A Gene, Muc, And Its Protein That Enhances Binding To Mucins In order to further identify strains of Lactobacilli with strong adhesive properties, work was done to identify a gene and its expressed protein that would enhance binding to intestinal cell surface proteins called mucins. Found and disclosed herein is a protein greater than 200 kD that enhances binding of *L. reuteri* to mucin. Subcloning and sequencing identified the muc gene.

Materials and Methods

In this experiment, the 1063 strain of *L. reuteri* was used to isolate the 200 kD proteins that provide for binding to mucins. The bacterial strains, growth conditions, reagents, construction and screening of the λ-library, and the affinity purification of the recombinant protein was as set forth in Example I. The mucin binding protein was isolated from the culture media as described herein.

Western Blotting:

Conducted as described in Example I. Primary antibody (p108) against the mucus binding protein was purified from a rabbit injected with the original solution of culture medium and water wash from strain 1063.

Mucin binding assay:

Partly purified mucin from porcine stomach obtained from Sigma (St. Louis, Mo.)was suspended in a carbonate buffer at pH 9.7 at a concentration of 0.1 mg/ml. 200 µl of the solution was pipetted into microtiter wells and were left for coating at 37° C. for approximately 3 hours. The wells were blocked by the addition of 200 µl of PBS 1% Tween20 at room temperature for 1 hour and then washed 3 times with PBST 0.5%Tween20 (PBST). Bacteria were grown in MRS broth overnight at 37° C., then washed and resuspended in PBST. Optical density (OD) of the bacterial cells was measured at 600 nm in a Beckman DU650 spectrophotometer and adjusted to OD 0.5. 150 µl of the bacterial suspension was loaded into triplicate wells and incubated at 37° C. for approximately 2 hours. Wells were washed 3 times and 200 µl/well of 1% SDS, 0.2 MNaOH was added and incubated for 15 minutes at room temperature. After gently mixing, 50 µl was taken in order to measure the amount of bound bacteria.

Inhibition Assay:

The affinity purified proteins from the different λ-clones were tested in the mucin binding assay. Prior to the addition of the bacteria to the wells, 10 µl of a solution of the purified protein with $A_{280}$=0.1 was added. The proteins were incubated for 30 minutes in the wells before the bacteria were added, without any washing of the well. The amount of bound bacteria were compared with a sample without addition of protein and also with a sample with addition of an equal amount of ovalbumin (Sigma). All samples were analyzed in triplicate.

Subcloning:

DNA from λ-clone 1208:21 was isolated, subcloned and positive clones were isolated as described in Example I.

DNA Sequencing and Analysis of the Sequence

Sequencing was performed by the dideoxy method, using ABI PRISM Dye Terminator Cycle Sequencing Ready Reaction Kit (Perkin-Elmer, Foster City, Calif., USA) with commercial standard and customized sequencing primers. The sequencing samples were analyzed on the automatic sequencing machine ABI 373 (Perkin-Elmer). The PC/GENE DNA and protein data handling package was used for analysis of the DNA and deduced protein sequence.

SDS-PAGE was conducted as set forth in Example I.

Results

Southern blotting:

The muc gene was found to be present in *L. reuteri* strain 1063.

Western blotting:

Mucin binding protein was observed only in the culture medium and not in the water wash.

The muc gene of *L. reuteri* strain 1063 was cloned and found to reside on a 6.2 kb EcoRI fragment. As described in Example I, different classes of clones were found when screening the λ-library with the antiserum. One class of clones expressed a <200 kDa protein that promoted adhesion of the bacteria to mucin. Subcloning of the DNA from one of these clones, λ108:21, into a plasmid vector allowed identification of clones reacting with the antisera and expressing a protein band of the same size as the λ-clone. One of these clones designated LrMu3 was harboring a 6.2 kb EcoRI fragment. Sequence analysis of the EcoRI fragment reveal an open reading frame preceded by a ribosome binding site and the possible transcription initiation signals. The nucleotide and amino acid sequences for the muc gene have been partially determined. They have been assigned the identifier Seq ID No: 2 in the Sequence Listing. Recombinant forms of strains that express a gene that promotes cellular aggregation, agg, and a gene mediating adherence to mucin, muc, as well as expressing foreign antigens on the cell surface are shown to be useful to vaccinate and thus protect the host against infection by the pathogenic microorganisms whose gene or genes have been inserted.

INDUSTRIAL APPLICABILITY

While the health benefits of vaccination against gastrointestinal pathogens are clear, finding safe and effective vaccines presents challenging problems. The disclosed discovery provides a method for vaccination of an animal with a microorganism containing genes that are responsible for the production of proteins that provide for the aggregation of individual cells and/or binding to mucosa cells and/or mucous and can be transformed so as to express foreign antigens.

The method of the invention described and claimed herein can be used in the pharmaceutical and food industries to prepare vaccines against pathogenic microorganisms or other biological material. The vaccine can be ingested by an animal in a pharmaceutically acceptable carrier or it can be added to milk or milk products such as yogurt. The vaccine can also be administered nasally or through other direct administration to mucosal tissues and/or mucous. Vaccination of an animal, with transformed Lactobacilli, preferably *L. reuteri*, as described herein serves to prevent or treat diseases immunologically associated with the host's mucosa.

While certain representative embodiments have been set forth herein, those skilled in the art will readily appreciate that modifications can be made without departing from the spirit or scope of the invention.

We claim:

1. An isolated and purified DNA segment having a DNA sequence as shown in Sequence ID No. 1 said DNA segment encoding a 60 kD protein mediating bacterial aggregation from *Lactobacillus reuteri*.

* * * * *